United States Patent [19]

Hargis

[11] Patent Number: 4,929,764

[45] Date of Patent: May 29, 1990

[54] ALKYLATION OF AROMATIC AMINES

[75] Inventor: Duane C. Hargis, Baton Rouge, La.

[73] Assignee: Ethyl Corporation, Richmond, Va.

[21] Appl. No.: 776,753

[22] Filed: Sep. 16, 1985

Related U.S. Application Data

[63] Continuation-in-part of Ser. No. 618,005, Jun. 6, 1984, Pat. No. 4,721,810.

[51] Int. Cl.$^5$ .............................................. C07C 85/24
[52] U.S. Cl. ..................................... 564/399; 564/409
[58] Field of Search .................................. 564/399, 409

[56] References Cited

U.S. PATENT DOCUMENTS 2,389,500  11/1945  Goshorn .............................. 260/585

FOREIGN PATENT DOCUMENTS 5390227  8/1978  Japan .

*Primary Examiner*—Charles F. Warren
*Attorney, Agent, or Firm*—John F. Sieberth

[57] ABSTRACT

By reacting a primary aromatic amine with a dialkyl ether in the presence of a titanium dioxide alkylation catalyst having a surface area below about 130 square meters per gram, preferably in the anatase crystallographic form, at a suitably elevated temperature above about 300° C., the amount of exclusively ring-alkylated product formed exceeds the amount of exclusively N-alkylated product formed.

15 Claims, No Drawings

ALKYLATION OF AROMATIC AMINES

REFERENCE TO RELATED APPLICATION

This is a continuation-in-part of prior copending application Ser. No. 618,005, filed June 6, 1984, now U.S. Pat. No. 4,721,810, Jan. 26, 1988.

FIELD

This invention relates to an improved catalytic process for the alkylation of aromatic amines.

BACKGROUND

Numerous methods, processes, and catalysts have been described for alkylating aromatic amines to provide valuable and useful chemical products. However, the previous suggestions have various defects including lack of selectivity of the desired product, poor conversion of the aromatic amine, and excessive deterioration of the alkylating agent which then cannot be recovered for recycle or other use.

Synthesis of products enriched in $C_2$–$C_4$ alkylated primary aromatic amines by catalytic alkylation of primary aromatic amines is difficult to accomplish, especially in a one pass vapor phase reaction using a heterogeneous catalyst. For example, as shown in my prior copending application Ser. No. 618,005, in the ethylation of aniline with diethyl ether using various B-subgroup metal oxide catalysts the amount of N-ethylaniline and N,N-diethylaniline normally exceeds the amount of exclusively ring ethylated anilines, such as o-ethylaniline, p-ethylaniline, and 2,6-diethylaniline. In fact in many cases it is possible by use of the process described in that copending application to achieve extremely high selectivity to N-alkylation by using under appropriate reaction conditions such metal oxide catalysts as $TiO_2$, $ZrO_2$, $ZnO$, $Ti_2O_3$, $TiO$, and the like. This is of course highly desirable and advantageous when it is desired to produce such N-alkylated products as N-ethylaniline, N,N-diethylaniline and the like. On the other hand there are situations in which it is desirable to produce a product in which the amount of exclusively ring-alkylated products exceeds the amount of product alkylated only on the nitrogen atom. One such process is described in the above copending application, and is dealt with with greater particularity herein.

THE INVENTION

In accordance with this invention an efficacious process for alkylating alkylatable aromatic amines is provided. In general, the process comprises the step of reacting (a) an aromatic amine having two replaceable hydrogen atoms on at least one amino group and at least one replaceable hydrogen atom on an aromatic ring carrying such amino group, with (b) an acyclic ether in the presence of a B-subgroup metal oxide alkylation catalyst so that alkylation of the aromatic amine occurs. For effecting nuclear alkylation (i.e., alkylation on the ring), best results are achieved when the aromatic amine has one primary amino group on an aromatic ring and has a replaceable hydrogen on the ring in at least an ortho or para position relative to such amino group.

More particularly, this invention involves using as the catalyst a metal oxide alkylation catalyst consisting essentially of titanium dioxide having a surface area below about 130 square meters per gram ($m^2/g$), preferably in the range of about 1 to about 125 $m^2/g$, and most preferably in the range of about 25 to about 125 $m^2/g$.

In addition, the alkylation is effected using as the alkylating agent a dialkyl ether, and preferably a dialkyl ether in which each alkyl group has 2 to 4 carbon atoms, and a reaction temperature above about 300° C. so that the amount of exclusively ring-alkylated product formed exceeds the amount of exclusively N-alkylated product formed. In many cases the process will be carried out at a temperature in the range of about 325°–450° C. While higher temperatures may be used, the temperature used should take into consideration the thermal decomposition temperatures of the reactants and products as well as the effect of temperature on the activity of the particular heterogeneous catalyst system being employed. In general, the most preferred temperatures for the process fall in the range of from about 350° to about 425° C.

This invention involves, inter alia, the discovery that titanium dioxide is capable of focusing a substantial portion of the alkylation either on the nitrogen atom or on the ring of alkylatable primary aromatic amines such as aniline, depending on its surface area and the reaction temperature used in the alkylation. With surface areas above about 130 $m^2/g$ alkylation with dialkyl ethers tends to be focused primarily on the nitrogen atom across the entire temperature range of about 200° to about 375° C. But with titanium dioxides with surface areas below about 130 $m^2/g$ it is possible to form products in which the quantity of ring-alkylated primary aromatic amines exceeds the quantity of exclusively N-alkylated aromatic amines, provided a suitably high reaction temperature is employed. For example in alkylating aniline with diethyl ether using $TiO_2$ with a surface area of 112 $m^2/g$, these results were readily achieved at 325° C., 350° C, 375° C., and 400° C. However at 250° C. and 300° C. the product contained a larger proportion of N-ethylaniline and N,N-diethylaniline than than these ring-alkylated anilines.

Preferably the titanium dioxide catalyst is in the anatase form, although other forms (e.g., a mixture of anatase and rutile forms) are deemed suitable in the process. Still other preferred embodiments of this invention will become apparent from the ensuing description and appended claims.

A particular advantage of my process is that under most reaction conditions employed much of the dialkyl ether alkylating agents such as diethyl ether not consumed in the alkylation reaction pass through the reaction zone undecomposed and thus can be readily recovered for recycle or other use. In addition, my process involves use of catalysts which are easily prepared, and which in many cases have superior catalytic activity and long useful lives.

Another feature of this invention is that the titanium dioxide catalyst need not be and preferably is not combined with other catalyst components, supports, or activators. However such materials may be used if desired so long as they do not materially detract from the efficacy of the titanium dioxide catalyst with which they are employed.

When the process is carried out as further described below, the conversion of the aromatic amines and the dialkyl ethers are quite satisfactory.

The process is suitably carried out at atmospheric pressure but may be conducted at superatmospheric or subatmospheric pressures. And it may be carried out in either a batch or continuous operation mode according to the available equipment and intentions of the operator.

Although the process can be carried out in the liquid phase, it is preferable to conduct the process in the vapor phase using a fixed-bed or a moving or fluidized bed of the catalyst.

Typical primary aromatic amines usable as reactants in the process include single ring primary monoamines such as aniline, o-toluidine, m-toluidine, p-toluidine, o-ethylaniline, m-ethylaniline, p-ethylaniline, o-isopropylaniline, m-isopropylaniline, p-isopropylaniline, 2,3-xylidine, 2,4-xylidine, 2,5-xylidine, 3,4-xylidine, 3,5-xylidine, 2,4-diethylaniline, 2,5-diethylaniline, 3,4-diethylaniline, 3,5-diethylaniline, 2,3-diisopropylaniline, 2,4-diisopropylaniline, 3,5-diisopropylaniline, and the like. Also usable are multiple ring mono- and polyamines such as 4-aminobiphenyl, 1-naphthylamine, 2-naphthylamine, 1-anthrylamine, 1,4-diaminonaphthalene, 1,5-diaminonaphthalene, 2,4-toluenediamine, 2,5-toluenediamine, 1,3-diaminobenzene, 4,4'-methylenebisaniline, and the like.

Of the above described aromatic amines, the single ring aromatic primary monoamines are preferred, especially aniline, one or a mixture of two or more toluidine isomers or one or a mixture of two or more xylidine isomers.

Dialkyl ethers where the alkyl groups are either the same or different, and preferably where at least one of them is a primary alkyl group, are suitable for use in the process. Thus use may be made of such ethers as dimethyl ether, dibutyl ether, ethyl propyl ether, ethyl octyl ether, diisobutyl ether, ethyl methyl ether, diisopropyl ether, heptyl methyl ether, methyl tert-butyl ether, and the like. Particularly preferred as alkylating agents in the process are diethyl ether, dipropyl ether, dibutyl ether, and diisobutyl ether.

It is important when practicing this invention to use an active alkylation catalyst for the process. In this connection, the thermal history of the catalyst appears to be of importance to its activity. For example, a highly active titania catalyst for the process of this invention with a surface area of 112 $m^2/g$ after having been heated to 450° C. was found to have lost a substantial amount of its catalytic activity for the process. And after heating the catalyst to 650° C., this catalyst was found to be totally ineffective in the process. Thus any given titanium dioxide catalyst may or may not be active in the process of this invention depending upon whether or not it was calcined and if so, whether the calcining temperature was high enough to destroy its catalytic activity for the process of this invention. Thus in selecting commercially available titanium dioxides for use in the process, one should attempt to secure materials that have not been calcined at excessively high temperatures that render them unsuitable in the present process. In cases where the manufacturers decline to supply such thermal history information, one should secure and test in the present process a variety of samples of candidate catalysts and select one or more having the best or optimum activity for the particular aromatic amine alkylation under consideration.

Methods for the manufacture of titanium dioxide are known and reported in the literature. When utilizing such procedures care should be taken to avoid heating the catalyst to a temperature which destroys or substantially diminishes its catalytic activity in the alkylation process.

The present invention will be still further understood by a review of the following illustrative examples of the best mode of the invention of which I am now aware, in which all of the percentages are expressed on a weight basis unless otherwise specified.

In the ensuing examples use was made of a tubular reactor positioned within an Ohio Thermal wire wound tubular furnace, model T11C-0432. The muffle tube of the furnace was 1½ inches inside diameter and 12 inches long, constructed of fused alumina. A ¼ inch inside diameter thermocouple well was provided adjacent to the heating element. The thermocouple was used to control the series 4DA controller which has a range of 200°–1100° C. The reactor itself was a 19 inch long, 1 inch inside diameter stainless steel tube fitted with an internal thermocouple well. The reactor tube was fitted for supply of helium gas from one line and a second line connected to a Milton Roy pump. The second line fed reactants from a reservoir attached thereto. A water condenser below the reactor tube and an ice bath were used to collect liquid in glassware in the ice bath. The vapors transmitted from the glassware in the ice bath were directed to a dry ice bath and the outlet thereof was connected directly to a gas chromatography unit and then to a wet test meter.

The following procedure was used for all of the runs given in the tables below. The reactor tube was filled with 5 millimeter glass beads to define the catalyst bed location. A weighed amount of catalyst was then supplied to the catalyst bed area and additional 5 millimeter beads were used to fill the tube to the top of the furnace. All equipment was properly purged and flushed according to good standard laboratory practice. The desired feed for the run was added to the reservoir and the pump and inlet tube as necessary. The ice water bath and dry ice bath were attached, and the helium flush was started at the rate of 20–30 cc per minute during furnace warmup and stabilization. To start a run, the helium was turned off, and the feed pump was turned on at the desired feed rate. The thermocouple temperatures were recorded along with the feed level and the wet test meter readings. The sampling times were also noted. The product gases were directed to the sample loop of the GC sampling valve and injected onto a $10' \times \frac{1}{8}''$ Poropak TM R column. The traps were removed and immediately replaced with a second set. The liquid samples were combined and weighed. To terminate the run, the feed pumps were turned off and drained for about five minutes before removing the residue therein. Thereafter, the helium flush was again turned on at about 20–30 cc per minute and the furnace was turned off. After cooling to room temperature, the reactor tube was removed for catalyst inspection, analysis, and/or replacement. The catalysts were unsupported—i.e., an inert support or carrier for the catalyst was not used in any of the runs. Except where otherwise noted, the operations were conducted using a liquid hourly space velocity (LHSV) of 0.2 $hr^{-1}$.

Table I summarizes the results of a number of runs at various temperatures using a variety of individual titanium dioxide catalysts in the vapor phase alkylation of aniline with diethyl ether. The reactants were employed in a ratio of 2.5 moles of diethyl ether per mole of aniline. The gaseous products referred to in the tables are uncondensables and the magnitude of this figure serves as an indication of the extent of decomposition, if any, that occurred during the run. All but one of the catalysts used in these runs were obtained from commercial sources, and are identified as follows:

Catalyst No. 21—$TiO_2$; Harshaw Ti-X-L2873-23-10. It was of the anatase crystallographic form and had a surface area of 143 $m^2/g$.

Catalyst No. 22—$TiO_2$; Harshaw Ti-0720. It was of the anatase crystallographic form and had a surface area of 112 $m^2/g$.

Catalyst No. 36—$TiO_2$; Harshaw Ti-X-L2873-23-10. It was of the anatase crystallographic form and had a surface area of 153 $m^2/g$.

The other catalyst referred to in Table I was synthesized as follows: Titanium isopropoxide (155.15 g) was dissolved in 200 mL of isopropanol and heated to 60° C. with stirring. Distilled water (42.5 mL) was added dropwise maintaining the temperature below 70° C. to precipitate titania. Excess isopropanol was evaporated off under a dry nitrogen stream at 50°-60° C. to give a thick paste. The paste was extruded through a 50 cc plastic syringe and air-dried overnight. The extrusions were oven-dried at 110° C. for 2 hours and then calcined at 450° C. overnight to give 41.7 g of finished catalyst. The catalyst had a surface area of 10.2 $m^2/g$, and was in the anatase crystallographic form.

TABLE I
Alkylations Using Titanium Dioxide Catalysts

| Run Number | 1 | 2 | 3 | 4 | 5 | 6 | 7 | 8 | 9 | 10 | 11 | 12 | 13 | 14 | 15* | 16 |
|---|---|---|---|---|---|---|---|---|---|---|---|---|---|---|---|---|
| Catalyst: | | | | | | | | | | | | | | | | |
| Number | 21 | 21 | 22 | 22 | 36 | 36 | 36 | 36 | 24 | 24 | 24 | 22 | 22 | 22 | 22 | 22 |
| Surface Area: $m^2/g$ | 143 | 143 | 112 | 112 | 153 | 153 | 153 | 153 | 10.2 | 10.2 | 10.2 | 112 | 112 | 112 | 112 | 112 |
| Temperature, °C. | 250 | 300 | 250 | 300 | 300 | 325 | 350 | 375 | 300 | 350 | 400 | 325 | 350 | 375 | 375 | 400 |
| Aniline Conversion, % | 54 | 87 | 69 | 95 | 59 | 70 | 71 | 64 | 38 | 88 | 68 | 95 | 91 | 86 | 71 | 65 |
| Ether Conversion, % | 18 | 45 | 19 | 61 | 22 | 35 | 54 | 72 | 9 | 60 | 99 | 77 | 93 | 98 | 76 | 96 |
| Product Distribution, wt. percent | | | | | | | | | | | | | | | | |
| N-et aniline | 64.4 | 38.2 | 51.9 | 16.7 | 63.7 | 52.8 | 51.5 | 51.5 | 82.7 | 50.0 | 22.0 | 11.5 | 5.1 | 3.3 | 26.5 | 12.0 |
| o-et aniline | 2.6 | 2.0 | 0.9 | 1.4 | 0.7 | 2.3 | 4.9 | 9.8 | 4.1 | 3.5 | 21.1 | 2.4 | 6.1 | 12.0 | 12.2 | 22.9 |
| p-et aniline | 4.5 | 1.9 | 3.5 | 3.4 | 0.9 | 1.3 | 1.6 | 2.3 | 4.5 | 1.3 | 9.2 | 4.1 | 6.2 | 8.8 | 7.8 | 10.6 |
| N,N-di-et aniline | 11.8 | 18.7 | 12.9 | 6.9 | 17.8 | 17.9 | 13.1 | 7.8 | 5.2 | 20.3 | 1.8 | 3.1 | 0.6 | 0.3 | 2.5 | 0.6 |
| 2,6-di-et aniline | 2.9 | 2.2 | 3.2 | 6.1 | 2.4 | 2.8 | 3.9 | 7.4 | — | 2.6 | 13.8 | 11.7 | 20.4 | 25.7 | 12.1 | 21.5 |
| Other ring di-et anilines | 7.1 | 17.1 | 12.9 | 22.8 | 8.8 | 13.5 | 15.3 | 11.9 | — | 14.2 | 11.8 | 17.1 | 7.9 | 4.4 | 13.8 | 5.6 |
| Ring tri-et anilines | 3.3 | 12.4 | 12.2 | 30.4 | 4.0 | 6.1 | 5.1 | 3.4 | — | 4.9 | 5.3 | 32.4 | 30.3 | 17.8 | 9.3 | 7.7 |
| Others | 3.3 | 7.6 | 2.5 | 12.3 | 1.6 | 3.2 | 4.5 | 5.9 | 3.5 | 3.2 | 15.0 | 17.7 | 23.6 | 27.8 | 15.8 | 19.0 |
| N-alkylation, % | 76.2 | 56.9 | 64.8 | 23.6 | 81.5 | 70.7 | 64.6 | 59.3 | 87.9 | 70.3 | 23.8 | 14.6 | 5.7 | 3.6 | 29.0 | 12.6 |
| Ring alkylation, % | 10.0 | 6.1 | 7.6 | 10.9 | 4.0 | 6.4 | 10.5 | 19.5 | 8.6 | 7.4 | 44.1 | 18.2 | 32.7 | 46.5 | 32.1 | 55.0 |
| Di-, tri-, & others, % | 13.7 | 37.1 | 27.6 | 65.5 | 14.4 | 22.8 | 24.8 | 21.2 | 3.5 | 22.3 | 32.1 | 67.2 | 61.8 | 50.0 | 38.9 | 32.3 |
| Ratio of o-et to p-et | 0.6 | 1.1 | 0.3 | 0.4 | 0.8 | 1.8 | 3.1 | 4.3 | 0.9 | 2.7 | 2.3 | 0.6 | 1.0 | 1.4 | 1.6 | 2.2 |
| Gaseous products, mL/hr | 5 | 55 | 0 | 75 | 20 | 70 | 200 | 400 | 25 | 205 | 600 | 225 | 315 | 410 | 670 | 730 |

*The LHSV was 0.4 per hour.

The results presented in Table I show that at suitably high temperatures the titania catalysts with surface areas below about 130 $m^2/g$ gave amounts of exclusively ring-alkylated product exceeding the amount of exclusively N-alkylated product formed. Table II summarizes these findings.

TABLE II

| | | Product Ratios | |
|---|---|---|---|
| Run No. | Surface Area | Temp °C. | Weight Ratio of Ring-Alkylated:N-Alkylated |
| 5 | 153 | 300 | 0.05 |
| 6 | 153 | 325 | 0.09 |
| 7 | 153 | 350 | 0.16 |
| 8 | 153 | 375 | 0.33 |
| 1 | 143 | 250 | 0.13 |
| 2 | 143 | 300 | 0.11 |
| 3 | 112 | 250 | 0.12 |
| 4 | 112 | 300 | 0.46 |
| 12 | 112 | 325 | 1.25 |
| 13 | 112 | 350 | 5.74 |
| 14 | 112 | 375 | 12.92 |
| 16 | 112 | 400 | 4.37 |
| 9 | 10.2 | 300 | 0.10 |
| 10 | 10.2 | 350 | 0.11 |
| 11 | 10.2 | 400 | 1.85 |

In contrast to the results reported in Table I, extensive amounts of decomposition of the alkylating agent were encountered when using an alcohol as the alkylating agent and an iron oxide-germanium oxide catalyst in accordance with the prior art. See in this connection U.S. Pat. No. 4,351,958. In particular, when ethanol and aniline were reacted in the above manner at 350° C. over a catalyst composed of 96.1 weight percent $Fe_2O_3$ and 3.9 weight percent $GeO_2$, non-condensable gases were evolved at the rate of 1800 mL/hr. In fact, no ethanol passed through the reaction zone—the ethanol which did not react with the aniline was completely destroyed.

The inclusion of water in the feed to the catalyst may be helpful insofar as the regiochemical aspects of the process are concerned. When water is employed, it will normally be used in amounts no higher than about 10 moles per mole of ether used, preferably in amounts falling in the range of about 0.1 to about 5 moles per mole of ether used.

The conditions used in the process of this invention are susceptible to variation. For example, while the process is usually conducted with an excess of the ether reactant relative to the aromatic amine reactant, a stoichiometric deficiency of the ether may be used, especially when seeking to maximize monoalkylation and minimize polyalkylation. Likewise, the ratio used will be influenced to some extent by the composition of the amine (i.e., whether it is a monoamine or a polyamine). In most cases, the reaction mixture will contain about 0.5 to about 5 molar equivalents of the ether per molar equivalent of the amine. In the case of reactions involving monoamines, the molar ratio of ether to amine is preferably in the range of about 1:1 to about 3:1.

It is possible to vary certain aspects and other features of the above described invention without departing from the lawful scope or true spirit thereof.

I claim:

1. A process for alkylating aromatic amines comprising the step of reacting (a) an aromatic amine having at least one replaceable hydrogen atom on a primary amino group and on an aromatic ring carrying such amino group, with (b) a dialkyl ether in which each alkyl group has 2 to 4 carbon atoms, in the presence of a metal oxide alkylation catalyst consisting essentially of titanium dioxide having a surface area below 130 square meters per gram and at a temperature in the range of 300° C. to 400° C. at which alkylation of the aromatic amine occurs and at which the amount of exclusively ring-alkylated product formed exceeds the amount of exclusively N-alkylated product formed.

2. A process of claim 1 wherein the ether is diethyl ether.

3. A process of claim 1 wherein the amine is a mononuclear primary aromatic amine having one or two amino groups on the aromatic ring.

4. A process of claim 3 wherein the amine is aniline, one or a mixture of two or more toluidine isomers or one or a mixture of two or ore xylidine isomers.

5. A process of claim 4 wherein the ether is diethyl ether.

6. A process of claim 1 wherein the reaction is conducted in the vapor phase by contacting a vapor phase mixture of the amine and the ether with a bed of the catalyst.

7. A process of claim 1 wherein the reaction is conducted at a temperature of at least about 325° C. but below that at which the catalyst becomes inactive.

8. A process of claim 1 wherein the catalyst is composed predominantly or entirely of titanium dioxide in the anatase crystallographic form.

9. A process for alkylating aromatic amines comprising the step of reacting (a) an aromatic amine having at least one primary amino group on an aromatic ring and having a replaceable hydrogen atom on the ring in at least an ortho or para position relative to such amino group, with (b) a dialkyl ether in which each alkyl group has 2 to 4 carbon atoms, in the presence of a metal oxide alkylation catalyst consisting essentially of titanium dioxide having a surface area below 130 square meters per gram and at a temperature in the range of 300° C. to 400° C. at which alkylation of the aromatic amine occurs and at which the amount of exclusively ring-alkylated product formed exceeds the amount of exclusively N-alkylated product formed.

10. A process of claim 9 wherein the ether is diethyl ether.

11. A process of claim 9 wherein the reaction is conducted in the vapor phase by contacting a vapor phase mixture of the amine and the ether with a bed of the catalyst at a temperature of at least about 325° C. but below that at which the catalyst becomes inactive.

12. A process of claim 11 wherein the amine is aniline, one or a mixture of two or more toluidine isomers or one or a mixture of two or more xylidine isomers, and the ether is diethyl ether, dipropyl ether or dibutyl ether.

13. A process of claim 11 wherein the catalyst is composed predominantly or entirely of titanium dioxide in the anatase crystallographic form.

14. A process of alkylating aromatic amines comprising the step of reacting (a) an aromatic amine having at least one replaceable hydrogen atom on a primary amino group and on an aromatic ring carrying such amino group, with (b) a dialkyl ether in which each alkyl group has 2 to 4 carbon atoms, in the presence of a metal oxide alkylation catalyst consisting essentially of titanium dioxide having a surface area of about 112 square meters per gram and at a temperature in the range of about 325° to about 400° C. so that alkylation of the aromatic amine occurs and so that the amount of exclusively ring-alkylated product formed exceeds the amount of exclusively N-alkylated product formed.

15. The process of claim 14 wherein the temperature is in the range of about 350° to about 400° C.

* * * * *